Figure 1:
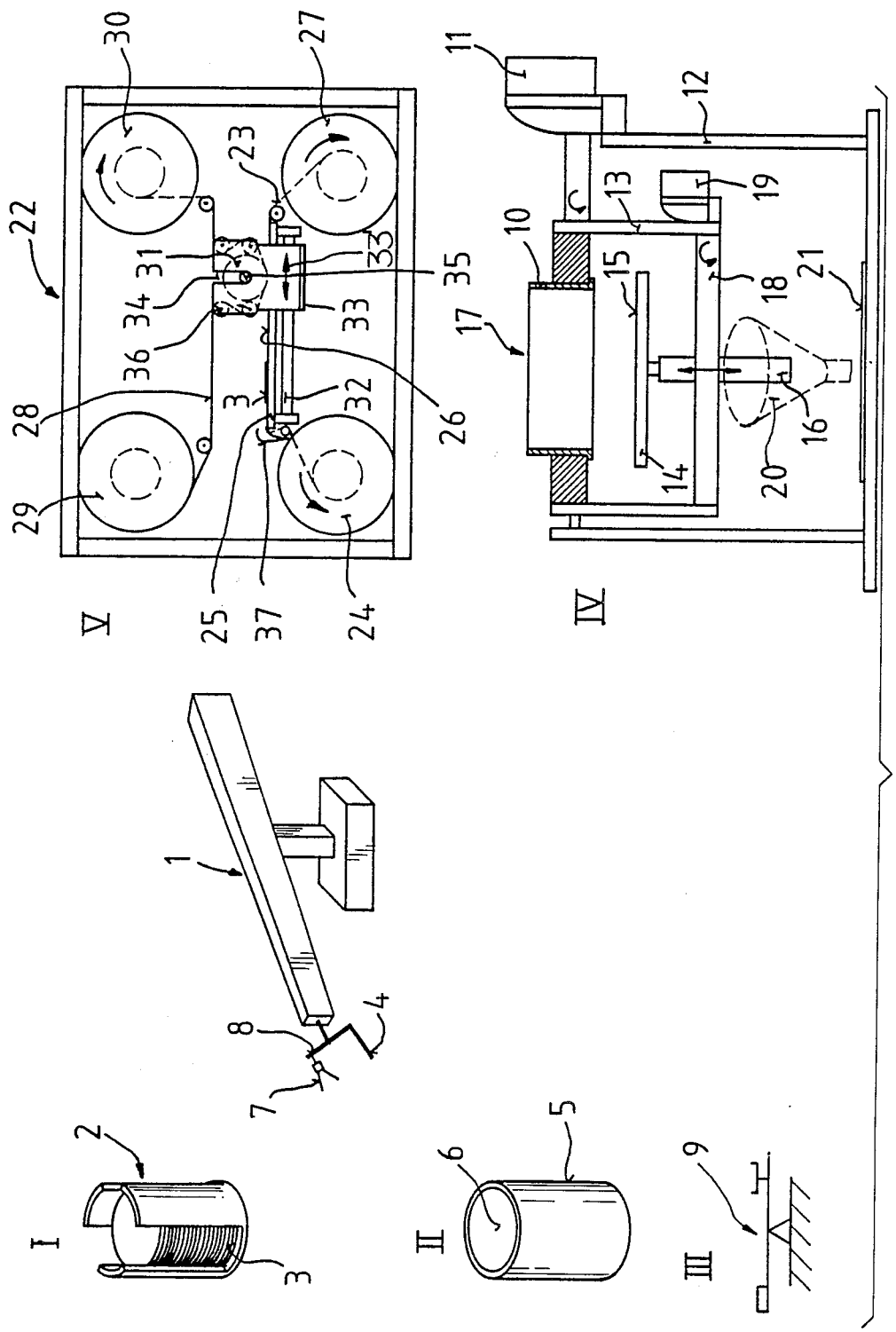

United States Patent [19]

Benninghoff et al.

[11] Patent Number: 4,976,138
[45] Date of Patent: Dec. 11, 1990

[54] MEASURING ARRANGEMENT FOR DETERMINING THE LIQUID ABSORPTION OF PAPER

[75] Inventors: Norbert Benninghoff, Mertesheim; Manfred Jaensch, Speyer; Jaroslav Melzer, Ludwigshafen; Gunter Niesar, Neuhofen; Werner Schuster, Hassloch, all of Fed. Rep. of Germany

[73] Assignee: BASF Aktiengesellschaft, Ludwigshafen, Fed. Rep. of Germany

[21] Appl. No.: 355,356

[22] Filed: May 23, 1989

[30] Foreign Application Priority Data

May 28, 1988 [DE] Fed. Rep. of Germany ....... 3818199

[51] Int. Cl.$^5$ ............................................. G01N 5/02
[52] U.S. Cl. .......................................... 73/73; 34/95.3
[58] Field of Search ................. 73/73, 76; 34/89.1, 34/95, 95.3, 9

[56] References Cited

U.S. PATENT DOCUMENTS

| | | | |
|---|---|---|---|
| 3,216,241 | 11/1965 | Hansen | 73/75 |
| 3,296,710 | 1/1967 | Krikorian | 34/95 |
| 3,325,909 | 6/1967 | Clark | 34/95 |
| 3,973,329 | 8/1976 | Feess | 34/95 |
| 4,259,862 | 4/1981 | Sheaks et al. | 73/73 |
| 4,509,361 | 4/1985 | Johnson | 73/73 |
| 4,771,631 | 9/1988 | Lehtikoski et al. | 73/73 |

FOREIGN PATENT DOCUMENTS

| | | | |
|---|---|---|---|
| 0102138 | 6/1984 | Japan | 73/73 |
| 0151740 | 7/1987 | Japan | 73/73 |
| 0983514 | 12/1982 | U.S.S.R. | 73/73 |

OTHER PUBLICATIONS

ISO, International Standard 535, Paper and Board—Determination of Water Absorption—Cobb Method, pp. 1–3, 1st Ed. (1976).

*Primary Examiner*—William A. Cuchlinski, Jr.
*Assistant Examiner*—Diego F. F. Gutierrez
*Attorney, Agent, or Firm*—Keil & Weinkauf

[57] ABSTRACT

The measuring arrangement consists of successive workstations which comprise a stock of paper samples, a balance, a mechanized moistening means for the sample and a blotting means, likewise mechanized, for the moistened sample. An industrial robot controllable by a program and equipped with a gripping apparatus is provided for carrying out the measurement. This arrangement determines the liquid absorbed by paper using the Cobb method and permits the measuring method to be carried out in a fully mechanized manner.

4 Claims, 1 Drawing Sheet

MEASURING ARRANGEMENT FOR DETERMINING THE LIQUID ABSORPTION OF PAPER

The present invention relates to a measuring arrangement for determining the liquid absorption of paper, consisting of successive workstations comprising a balance for a paper sample, a moistening means for the paper sample, which is formed by a metal cylinder and a plate which, together with the paper sample, is capable of sealing off said cylinder and a blotting means having an upper and a lower blotting board enclosing the paper sample, and a blotting roll.

The Cobb method and apparatus therefor for determining the liquid absorbed by paper and board are laid down in DIN 53132 or ISO 535-1976. The above-described measuring arrangement constructed in accordance therewith only permits the measuring method to be carried out manually. Apart from being very labor-intensive and time-consuming, the method has the disadvantage that the result of the measurement depends to a very great extent on the accuracy of the individual steps and hence on the particular operator.

It is an object of the present invention to provide a measuring arrangement for a measuring method according to the abovementioned standard specification, which permits the measuring method to be carried out in a fully mechanized manner.

We have found that this object is achieved by a measuring arrangement corresponding to the construction described at the outset and having the following features:

- a means which is controllable by a program and drivable in the spatial coordinate system toward the individual workstations and has a gripping apparatus,
- a store for the paper samples which is arranged upstream of the balance,
- the metal cylinder and the plate are drivable toward one another by means of a working cylinder, the metal cylinder being swivelably mounted, and the upper and lower blotting boards, each in the form of a web connected to a material feed means, are guided over a support area, the blotting roll being unrollable on the upper web by means of a reversing drive.

The novel measuring arrangement is described in detail below with reference to an embodiment shown schematically in the drawing.

The central part of the measuring arrangement is a means 1 which is controllable by a program and can be driven in the spatial coordinate system (X, Y, Z) toward the individual workstations I–V grouped around the said part. For this purpose, a commercially available industrial robot having the relevant control is used, the said control being described in more detail in the relevant instrument documents.

The workstation I is formed by a store 2, for example a laterally open cylinder, for circular paper samples 3, from which cylinder the means 1 removes a sample with the aid of a suction gripper 4. In the workstation II, the sample is placed on the edge of a further cylinder 5 having a central opening 6 so that, after the suction at the gripper has been switched off, a small interleaf for separation from the sample can fall into this opening. The sample is then gripped by a mechanical gripper 7, which is mounted together with the suction gripper on a turnover plate 8 of the means 1 (robot head), and is placed on the plate of a commercial electronic paper balance 9 in workstation III.

After weighing and storage of the result of the weighing, the sample is brought by means of gripper 7 to workstation IV, where a moistening means is located. It consists of a metal cylinder 10 which is fastened in a frame 13, which is swivelable by a drive 11 in a frame 12, and a plate 14, which is provided with a rubber cover 15 and can be driven toward the metal cylinder 10 by means of a pneumatic working cylinder 16 to form a container 17 closed at the base. The working cylinder 16 is held on a shaft 18, rotatable in the frame 13, and can be swiveled through 180° by a drive 19. After the paper sample has been placed on the rubber cover 15 of the plate 14 by the gripper 7, the plate 14 with the sample is pressed by the working cylinder 16 against the lower edge of the metal cylinder 10, so that the latter is tightly sealed. A defined amount of water is poured into the container 17 via a spray not shown in the drawing and is thus brought into contact with the paper sample. After an agreed contact time, the water is poured off by swiveling the frame 13 with the container 17 by means of the drive 11 to such an extent that the water can flow into a discharge funnel 20. The frame then swivels back, whereupon the plate is driven back and the moistened sample can be brought by the gripper 7 of the means 1 to a blotting means in workstation V. In the meantime, the drive 19 rotates the working cylinder 16 with the plate 14 180° downward, so that the plate can be pressed against a blotting board 21 to dry the rubber cover 15. It is advantageous if a material web which can be fed from a reserve is provided for the blotting board.

In the blotting means 22, the paper sample 3 is placed on a lower blotting board web 23, which is guided from a stock roll 24 over a table 25 providing a support area 26 to a takeup roll 27. Above the support area, a second upper blotting board web 28 is stretched parallel to the said web, likewise between a stock roll 29 and a takeup roll 30. To blot off the sample, the upper blotting board web is brought into contact with the sample by means of a blotting roll 31, which rolls several times, under its own weight, over the covered sample. A carriage 33 which is mounted on two guide rails 32 so that it can be horizontally displaced and which loosely accommodates the axle 35 of the blotting roll 31 in a vertical bearing groove 34 is provided for this purpose. The blotting board web is guided around the blotting roll 31 by means of guide rolls 36. The carriage is driven by a conventional reversing drive not shown in greater detail in the drawing, for example a continuous toothed belt to which the slide is fastened and which is driven by a motor whose direction of rotation can be changed. The reversing drive has been schematically indicated in the drawing by the double arrow 33'.

After the blotting process, the carriage 33 is once again in the starting position, in which the blotting board web 23 is not subjected to a load by the blotting roll 31, owing to a depression in the table 25. The blotting board web can then be driven back toward the stock roll 24 in order to convey the paper sample into a pocket 37, from which it is removed by the gripper 7 of the means 1 and once again conveyed to the balance 9. The liquid absorption is then obtained from the subsequent weighing and the weighing carried out at the beginning. The paper sample is then conveyed to a deposition point. To prepare two new blotting board sections for the next measuring cycle, the takeup rolls 27 and 30 finally transport the webs 23 and 28 in the feed direction.

Driving of the stock roll 24 for conveying the lower web 23 backward and driving of the takeup roll 27 are each effected by an electric motor which is not shown in the drawing and which can be connected to the respective roll shaft via commercially available coupling means. For the upper blotting board web 28, an identical drive is required only for the takeup roll 30.

The control for the measuring sequence described above does not form part of the subject-matter of the present invention but is conventional, so that it need not be described in detail.

We claim:

1. A measuring arrangement for determining the liquid absorption of paper, comprising
   a means which has a gripping apparatus and which is controllable by a program and is sequentially drivable in the spatial coordinate system toward a plurality of individual workstations, said workstations including a store and downstream thereof a balance for a paper sample, a moistening means for the paper sample and a blotting means,
   said moistening means including a metal cylinder and a plate which, together with the paper sample, is capable to seal off said cylinder, said cylinder and said plate being driven toward one another by means of a working cylinder, and
   said blotting means having a blotting roll and an upper and lower blotting board including said sample and each being in the form of a web connected to a material feed means and each being guided over a support area, the blotting roll being unrollable on the upper web by means of a reversing drive.

2. A measuring arrangement as claimed in claim 1, wherein the controllable means which can be driven toward the individual workstations is an industrial robot.

3. A measuring arrangement as claimed in claim 1, wherein the plate associated with the metal cylinder can be swiveled through 180° by a drive and can thus be driven with the aid of a working cylinder alternately toward the metal cylinder or toward a blotting board.

4. A measuring arrangement as claimed in claim 1, wherein the upper and lower blotting board webs are guided a distance apart and parallel to the support area, and the upper web is guided around the blotting roll which is loosely mounted vertically in a carriage and rests on the support.

* * * * *